(12) United States Patent
Ratron et al.

(10) Patent No.: US 8,114,091 B2
(45) Date of Patent: Feb. 14, 2012

(54) SURGICAL INSTRUMENTATION KIT FOR INSERTING AN ANKLE PROSTHESIS

(75) Inventors: Yves-Alain Ratron, Grenoble (FR); Jean-Emmanuel Cardon, Brignoud (FR); Thierry Judet, Ville d'Avray (FR); Jean-Alain Colombier, Balma (FR); Michel Bonnin, Lyons (FR)

(73) Assignee: Tornier, Saint-Ismier (FR)

( * ) Notice: Subject to any disclaimer, the term of this patent is extended or adjusted under 35 U.S.C. 154(b) by 863 days.

(21) Appl. No.: 11/626,735

(22) Filed: Jan. 24, 2007

(65) Prior Publication Data

US 2007/0173947 A1 Jul. 26, 2007

Related U.S. Application Data

(60) Provisional application No. 60/762,139, filed on Jan. 26, 2006.

(30) Foreign Application Priority Data

Jan. 24, 2006 (FR) .................................. 06 00644

(51) Int. Cl.
*A61B 17/58* (2006.01)
*A61B 17/60* (2006.01)
*A61F 2/00* (2006.01)
*A61F 2/42* (2006.01)

(52) U.S. Cl. ...................... 606/99; 606/86 R; 623/21.18

(58) Field of Classification Search .................... 606/99; 623/21.18

See application file for complete search history.

(56) References Cited

U.S. PATENT DOCUMENTS

| 5,171,289 | A | 12/1992 | Tornier |
| 5,314,485 | A | 5/1994 | Judet |
| 5,326,359 | A | 7/1994 | Oudard |
| 5,358,526 | A | 10/1994 | Tornier |
| 5,405,399 | A | 4/1995 | Tornier |
| 5,429,639 | A | 7/1995 | Judet |
| 5,458,650 | A | 10/1995 | Carrett et al. |

(Continued)

FOREIGN PATENT DOCUMENTS

DE 10123124 C1 12/2002

(Continued)

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner* — Thomas C. Barrett
*Assistant Examiner* — David Bates
(74) *Attorney, Agent, or Firm* — Faegre Baker Daniels LLP (57) ABSTRACT

A surgical instrument including at least one tibial phantom generally corresponding to at least certain features of the tibial implant. The tibial phantom includes a top surface adapted to move freely against the prepared bottom end of the tibia. At least one talus phantom generally corresponding to at least certain features of the talus implant is engaged with the prepared top surface of the talus. At least one phantom skid is located between the tibial phantom and the talus phantom. The phantom skid is engaged with the tibial phantom such that dynamic engagement between the phantom skid and the talus phantom through at least extension and flexion of the ankle joint positions the tibial phantom on the prepared bottom end of the tibia. The phantom skid can either be a part of the tibial phantom or a separate component.

38 Claims, 7 Drawing Sheets

U.S. PATENT DOCUMENTS

| | | | |
|---|---|---|---|
| 5,505,731 A | 4/1996 | Tornier | |
| 5,591,168 A | 1/1997 | Judet et al. | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,766,256 A | 6/1998 | Oudard et al. | |
| 5,824,106 A | 10/1998 | Fournol | |
| 5,879,395 A | 3/1999 | Tornier et al. | |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,203,575 B1* | 3/2001 | Farey | 623/18.11 |
| 6,206,925 B1 | 3/2001 | Tornier | |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,379,387 B1 | 4/2002 | Tornier | |
| 6,409,767 B1* | 6/2002 | Perice et al. | 623/21.18 |
| 6,454,809 B1 | 9/2002 | Tornier | |
| 6,488,712 B1 | 12/2002 | Tornier et al. | |
| 6,540,770 B1 | 4/2003 | Tornier et al. | |
| 6,582,469 B1 | 6/2003 | Tornier | |
| 6,599,295 B1 | 7/2003 | Tornier et al. | |
| 6,626,946 B1 | 9/2003 | Walch et al. | |
| 6,761,740 B2 | 7/2004 | Tornier | |
| 6,767,368 B2 | 7/2004 | Tornier | |
| 6,802,864 B2 | 10/2004 | Tornier | |
| 6,824,567 B2 | 11/2004 | Tornier et al. | |
| 6,890,357 B2 | 5/2005 | Tornier | |
| 6,969,406 B2 | 11/2005 | Tornier | |
| 7,025,790 B2* | 4/2006 | Parks et al. | 623/21.18 |
| 7,033,396 B2 | 4/2006 | Tornier | |
| 7,323,012 B1* | 1/2008 | Stone et al. | 623/21.18 |
| 7,749,276 B2* | 7/2010 | Fitz | 623/20.18 |
| 2003/0009170 A1 | 1/2003 | Tornier | |
| 2003/0009171 A1 | 1/2003 | Tornier | |
| 2003/0028198 A1 | 2/2003 | Tornier et al. | |
| 2003/0181985 A1* | 9/2003 | Keller et al. | 623/21.18 |
| 2004/0030399 A1* | 2/2004 | Asencio | 623/21.18 |
| 2004/0078079 A1* | 4/2004 | Foley | 623/17.11 |
| 2004/0134821 A1 | 7/2004 | Tornier | |
| 2004/0210220 A1 | 10/2004 | Tornier | |
| 2004/0230197 A1 | 11/2004 | Tornier et al. | |
| 2005/0049709 A1 | 3/2005 | Tornier | |
| 2005/0055102 A1 | 3/2005 | Tornier et al. | |
| 2005/0165490 A1 | 7/2005 | Tornier | |
| 2005/0182492 A1* | 8/2005 | Pappas et al. | 623/21.18 |
| 2005/0203536 A1 | 9/2005 | Laffargue et al. | |
| 2005/0278030 A1 | 12/2005 | Tornier et al. | |
| 2005/0278031 A1 | 12/2005 | Tornier et al. | |
| 2005/0278032 A1 | 12/2005 | Tornier et al. | |
| 2005/0278033 A1 | 12/2005 | Tornier et al. | |
| 2005/0288791 A1 | 12/2005 | Tornier et al. | |
| 2005/0288792 A1* | 12/2005 | Landes et al. | 623/21.18 |
| 2006/0015185 A1 | 1/2006 | Chambat et al. | |
| 2006/0142870 A1* | 6/2006 | Robinson et al. | 623/21.18 |
| 2006/0173457 A1 | 8/2006 | Tornier | |
| 2006/0235538 A1 | 10/2006 | Rochetin et al. | |
| 2007/0112431 A1* | 5/2007 | Kofoed | 623/21.18 |
| 2009/0054992 A1* | 2/2009 | Landes et al. | 623/21.18 |
| 2009/0132045 A1* | 5/2009 | Lafosse | 623/14.12 |
| 2009/0182433 A1* | 7/2009 | Reiley et al. | 623/18.11 |

FOREIGN PATENT DOCUMENTS

| | | |
|---|---|---|
| FR | 2759900 A1 | 8/1998 |
| WO | WO 00/69373 | 11/2000 |
| WO | WO 01/89427 | 11/2001 |

OTHER PUBLICATIONS

Rochetin et al., U.S. Appl. No. 11/401,415, entitled "Surgical Apparatus for Implantation of a Partial or Total, " filed Apr. 11, 2006.

Rochetin, U.S. Appl. No. 11/670,274, entitled "Offset Stem Tibial Implantation," filed Feb. 1, 2007.

\* cited by examiner

SURGICAL INSTRUMENTATION KIT FOR INSERTING AN ANKLE PROSTHESIS

CROSS-REFERENCE TO RELATED APPLICATIONS

The present application claims priority to prior French Application No. 0600644, filed Jan. 24, 2006, entitled Ensemble D'instrumentation Chirurgicale pour poser une prothese de Cheville. The present application also claims the benefit of U.S. Provisional Application No. 60/762,139 filed Jan. 26, 2006, entitled Ensemble D'instrumentation Chirurgicale pour poser une prothese de Cheville. The entire specification of both applications noted-above are hereby incorporated by reference.

FIELD OF THE INVENTION

The present invention relates to a surgical instrumentation kit and associated method for implanting an ankle prosthesis.

BACKGROUND OF THE INVENTION

An ankle prosthesis mainly includes a tibial implant, a talus implant, and a prosthetic skid interposed between the tibial and talus implants. The prosthetic skid is said to be "moving" when it is assembled to the tibial and talus implants so as to be movable relative to both of them, whereas the prosthetic skid is the to be "stationary" when, while still being movable relative to the talus implant, it is secured in stationary manner to the tibial implant.

During a surgical intervention by an anterior approach path, putting a moving-plate or a stationary-plate prosthesis into place in the ankle of a patient requires the bottom end of the tibia and the top end of the talus of the patient to be prepared, in particular by resections, so as to make it possible to secure the tibial and talus implants permanently thereto. In practice, once these bone preparation operations have been performed, the surgeon frequently makes use of test components or "phantoms" generally corresponding to at least some aspects of the corresponding prosthetic implants, thus making it possible to verify that the preparation operations are appropriate and that there is no need for additional bone removal or additional resurfacing.

Thus, the surgeon puts into place, in the ankle of the patient: a phantom corresponding to the talus implant, which phantom is held in place on the resected end of the talus; a phantom corresponding to the tibial implant, which phantom is held in place by being pressed against the resected end of the tibia; and a phantom skid corresponding to the prosthetic skid, which phantom skid is interposed between the talus and tibial implant phantoms and movable relative to each of the implant phantoms.

The surgeon typically has a plurality of phantom skids available of different respective thicknesses, with each of the phantom skids corresponding to a prosthetic skid suitable for being implanted subsequently. The surgeon selects the phantom skid having the thickness that is the most appropriate. Depending on the morphology of the patient, on the pathology that requires a prosthesis to be put into place, and/or on the relative positioning of the resections performed, the thickness of the skid that will actually be implanted can vary (i.e. its dimension in a generally vertical direction can vary), so that in practice the surgeon has available a series of several prosthetic skids each presenting substantially the same moving or stationary connection surfaces relative to the talus and tibial implants, but with respective thicknesses equal to about 4 millimeters (mm), about 5 mm, about 6 mm, and about 7 mm, for example.

After the above-mentioned phantom components have been put into place, the surgeon moves the ankle joint of the patient, in particular with flexion-extension movements. The surgeon can then act, in preoperative mode, to verify the quality with which the bones have been prepared, and also the dynamic behavior of the ankle provided with the phantom components, which is representative of the dynamic behavior the ankle will subsequently have, once fitted with the prosthetic components that are to be implanted.

In spite of the structural qualities of ankle prostheses, clinical hindsight shows that such ankle prostheses are implanted quite frequently in unsatisfactory manner. For example, for a stationary skid prosthesis, significant excess stress is to be observed in service between the skid and the tibial implant, which leads in the fairly short term to the stationary connection zone between the implant and the skid breaking, or to damage to the end of the tibial bone. With regard to moving skid prostheses, which specifically tend to be used to overcome the above-mentioned drawback of stationary skid prostheses, it is found in service that the top surface of the prosthetic skid extends to a greater or lesser extent outside the peripheral outline of the bottom surface of the tibial implant, such that the portions of these surfaces that are in moving contact are smaller than intended, leading to premature wear of the skid and/or of the implant. In other words, the insertion methods currently in use do not guarantee effective relative positioning between the tibial implant and the prosthetic skid, regardless of whether the skid is stationary or moving, since no reliable correction option is made available to the surgeon.

BRIEF SUMMARY OF THE INVENTION

The present invention is directed to a surgical instrument for implanting at least a tibial prosthesis on a prepared bottom end of a tibia and at talus prosthesis on a prepared top surface of a talus of an ankle joint.

One embodiment of the surgical instrument includes at least one tibial phantom generally corresponding to at least certain features of the tibial implant. The tibial phantom includes a top surface adapted to move freely against the prepared bottom end of the tibia. At least one talus phantom generally corresponding to at least certain features of the talus implant is engaged with the prepared top surface of the talus. At least one phantom skid is located between the tibial phantom and the talus phantom. The phantom skid is engaged with the tibial phantom such that dynamic engagement between the phantom skid and the talus phantom through at least extension and flexion of the ankle joint positions the tibial phantom on the prepared bottom end of the tibia.

Moving the ankle joint of the patient while the phantom components are placed therein provides the surgeon with reliable information concerning the precise position of the tibial phantom against the resected end $T_1$ of the tibia. This position is satisfactory or even optimum from the point of view of subsequent dynamic behavior of the ankle prosthesis. The dynamic engagement between the phantom skid and the talus phantom preferably self-positions the tibial phantom on the prepared bottom end of the tibia in a precise anatomical location corresponding to an optimum operation of the ankle joint.

The tibial phantom and the phantom skid can be separate components or a single component. The tibial phantom preferably slides on the prepared bottom end of the tibia during extension and flexion of the ankle joint. A low friction coating is optionally located on the top surface of the tibial phantom. In another embodiment, a biocompatible lubricant located between the top surface of the tibial phantom and the prepared bottom end of the tibia.

In some embodiments, the extension and flexion of the ankle joint moves a midplane of the tibial phantom to an angle a relative to a sagittal plane $T_3$ of the ankle joint. The upper surface of the talus phantom and a bottom surface of the phantom skid preferably include complementary surfaces that simulate movement of the talus implant and a prosthetic skid in the ankle joint.

The surgical instrument preferably includes an alignment member that is simultaneously positioned relative to the tibia during positioning of the tibial phantom. In one embodiment, the alignment member is engaged with the tibial phantom and includes a drill guide adapted to prepare the tibia to receive the tibial prosthesis. In another embodiment, the alignment member is positioned opposite an anterior face of the tibia.

The alignment member can also measure a setback of the tibial phantom relative to a surface of the tibia. The alignment member preferably measures a setback ($\delta_p$) of the tibial phantom relative to an anterior surface of the tibia. In one embodiment, at least a portion of the alignment guide and the tibial phantom comprising a single component. In one embodiment, displacement of a midplane of the tibial phantom to an angle a relative to a sagittal plane ($T_3$) of the ankle joint results in a medio-lateral offset ($\delta_\alpha$) of the alignment member along an anterior face of the tibia.

One embodiment of the present surgical instrument is directed to a kit including a plurality of tibial phantoms, a plurality of talus phantoms, and/or a plurality of phantom skids. Another embodiment is directed to an impacting instrument that locates the tibial prosthesis at a setback from a surface of the tibia as measured by the surgical instrument.

In another embodiment, the surgical instrument includes at least one tibial phantom generally corresponding to at least certain features of the tibial implant. The tibial phantom includes a top surface adapted to move freely against the prepared bottom end of the tibia. At least one alignment member is engaged with the tibial phantom. At least one talus phantom generally corresponding to at least certain features of the talus implant is engaged with the prepared top surface of the talus. Dynamic engagement between the tibial phantom and the talus phantom through at least extension and flexion of the ankle joint positions the tibial phantom on the prepared bottom end of the tibia and positions the alignment member relative to a surface of the tibia.

Another embodiment is directed to a surgical method for implanting at least a tibial prosthesis on a prepared bottom end of a tibia and at talus prosthesis on a prepared top surface of a talus of an ankle joint. The method includes locating at least one tibial phantom generally corresponding to at least certain features of the tibial implant on the prepared bottom end of the tibia. At least one talus phantom generally corresponding to at least certain features of the talus implant is located on the prepared top surface of the talus. A phantom skid is located between the tibial phantom and the talus phantom. The ankle joint is moved through at least flexion and extension, such that dynamic engagement between the phantom skid and the talus phantom positions the tibial phantom on the prepared bottom end of the tibia. The position of the tibial phantom against the prepared bottom end of the tibia is identified and the tibial implant is implanted in the identified position.

Dynamic engagement between the phantom skid and the talus phantom preferably simulates movement of the talus implant and a prosthetic skid in the ankle joint. The tibial phantom preferably slides on the prepared bottom end of the tibia during extension and flexion of the ankle joint. Consequently, the tibial phantom is displaced to the optimum location on the prepared surface of the tibia that most closely approximates natural movement of the ankle joint.

In one embodiment, an alignment member is simultaneously positioned relative to the tibia during positioning of the tibial phantom. The tibia is preferably prepared to receive the tibial prosthesis using the alignment member engaged with the tibial phantom. The alignment member is preferably at least a drilling guide. In another embodiment, the alignment member also measures an offset of the tibial phantom relative to a surface of the tibia, such as for example the anterior surface. In one embodiment, displacement of a midplane of the tibial phantom to an angle a relative to a sagittal plane ($T_3$) of the ankle joint results in a medio-lateral offset ($\delta_\alpha$) of the alignment member along an anterior face of the tibia.

During the surgical operation for implanting an ankle prosthesis, regardless of whether it is a fixed skid or a moving skid prosthesis, the surgeon puts the tibial phantom, the talus phantom, and the phantom skid of the instrumentation kid of the invention into place in the previously prepared ankle of the patient prior to final implantation of the prosthesis. Thereafter, the surgeon, still in preoperative mode, moves the ankle joint of the patient, in particular to make sure that the bones have been prepared in satisfactory manner and that the size of the prosthetic skid to be implanted is suitable, and possibly also that the sizes of the tibial implant and/or of the talus implant are suitable.

During this movement of the joint, there is preferably no freedom of movement between the phantom skid and the tibial phantom. The tibial phantom, however, can be moved freely against the bottom end of the tibia of the patient. As a result, the phantom skid positions the tibial phantom to an optimal position on the prepared surface of the tibia. Using the position of the tibial phantom as a guide, the location for the tibial implant is determined.

Depending on whether the subsequently implanted prosthetic skid is of the stationary type or is of the moving type, it will thus be understood that by ensuring that the tibial phantom and the phantom skid are connected to each other in stationary manner in the same configuration as the stationary assembly of the tibial implant and of the prosthetic skid as subsequently implanted, it is ensured that the phantom skid is centered overall on the bottom surface of the tibial phantom, so that the subsequently implanted prosthetic skid is likewise either assembled without excess stress to the tibial implant, or else is generally centered against the bottom surface of the tibial implant.

In practice, in order to ensure satisfactory relative positioning between firstly the tibial phantom and the phantom skid connected together in stationary manner, and secondly the talus phantom, the talus phantom is advantageously adapted to present behavior in movement relative to the phantom skid and to the talus of the patient that is analogous, at least in part, to the movements of the talus implant relative to the prosthetic skid and the talus of the patient.

As a result, when the talus phantom is put into place and secured to the top end of the talus of the patient and the phantoms of the instrumentation kit of the invention are moved in preoperative mode, the phantom skid hinges against the talus phantom, at least in part, with the same movement as will occur between the talus implant and the prosthetic skid once they have been implanted. In other words, the implantation position for the tibial implant, as obtained by the surgeon in the manner explained above, takes account of the implantation position of the talus implant of the prosthesis.

Advantageously, the joint surfaces of the talus phantom and of the phantom skid adapted for co-operating with each other are complementary to each other in horizontal section. In this way, medio-lateral movement is limited or prevented between the phantom skid and the talus phantom during the preoperative movement of the phantom components in the ankle of the patient, thus avoiding any disturbance to the relative medio-lateral positioning between the bottom end of the tibia and the subassembly constituted by the phantom skid and the tibial phantom while they are secured to each other.

The method of the invention enables the surgeon to determine a position for implanting the tibial implant that is satisfactory in that the implantation position guarantees predetermined co-operation between the tibial implant and the prosthetic skid as subsequently implanted. When the prosthetic skid is stationary, that co-operation corresponds to a stationary connection without excess stress. That co-operation corresponds to a moving connection generally centered against the bottom face of the tibial implant.

BRIEF DESCRIPTIONS OF THE SEVERAL VIEWS OF THE DRAWING

The invention can be better understood on reading the following description given purely by way of example and made with reference to the drawings, in which.

DETAILED DESCRIPTION OF THE INVENTION

Figure 1:
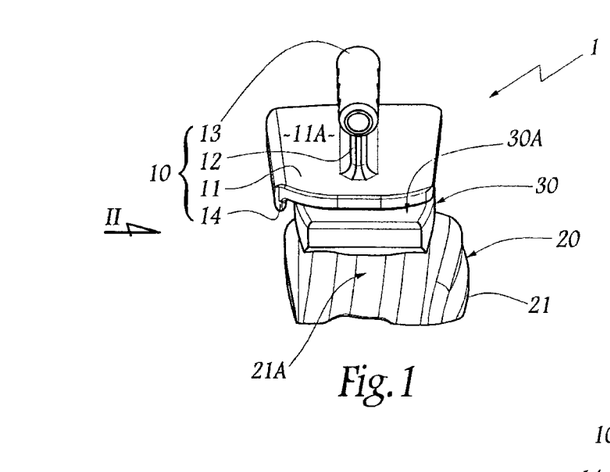
FIG. 1 illustrates an exploded view of an exemplary ankle prosthesis suitable for use with the instrumentation kit in accordance with the present invention.
Figure 2:
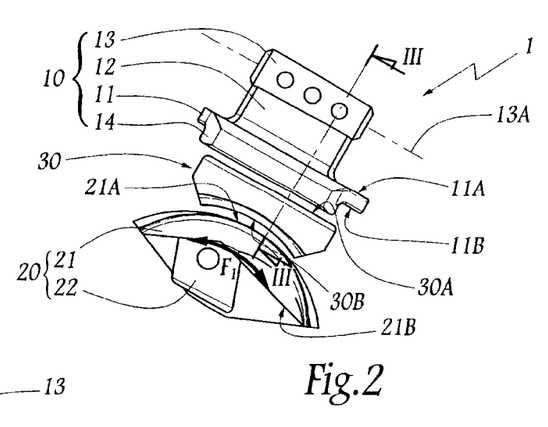
FIG. 2 is a side view of the exemplary ankle prosthesis of FIG. 1.
Figure 3:
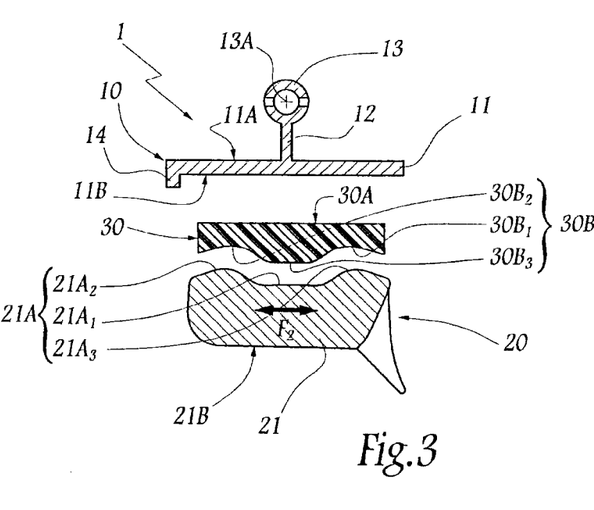
FIG. 3 is a sectional view of the exemplary ankle prosthesis of FIG. 2.

FIGS. 1 to 3 show an example of a "moving skid" ankle prosthesis. The prosthesis comprises three distinct components for implanting in the place of a right ankle joint of a human being, namely a tibial implant 10, a talus implant 20, and a prosthetic skid 30. For convenience, the description below describes directions relative to the bones of an ankle in their anatomical position, i.e. the terms "posterior" or "rear", "anterior front", "right", "left", "upper", "lower", etc. should be understood relative to the ankle of a patient standing on a substantially horizontal surface. Similarly, the term "sagittal" corresponds to a direction in the antero-posterior direction vertically on the mid-line of the ankle, while the term "medial" corresponds to a direction substantially perpendicular to the sagittal plane of the ankle, and directed towards the ankle, with the term "lateral" corresponding to the opposite direction.

The tibial implant 10 comprises a plate 11 for securing to the bottom end of the patient's right tibia, after the end has been suitably prepared. In the illustrated embodiment, the plate 11 is integrally molded via its top face 11A via a sagittal fin 12 with a hollow bone anchor stud 13 presenting an outside shape that is generally cylindrical with a circular base on an axis 13A that extends in a generally antero-posterior direction. Other bone anchor mechanism can be envisaged for the plate 11 providing they hold the tibial implant effectively at the bottom end of the tibia.

On its medial side, the plate 11 is provided with a rim 14 extending downwards in a generally vertical plane and suitable for bearing, at least in part, against the medial malleolus of the tibia, via the inside of the malleolus. On the inside, the plate 11 defines a plane surface 11B to form a surface for sliding against the plane top surface 30A of the skid 30.

In the illustrated embodiment, the talus implant 20 includes main block 21 for securing to the top end of the right talus of the patient, via a hollow stud 22 or any other suitable mechanism extending downwards from the bottom face 21B of the block 21. On its top face, the block 21 defines a joint surface 21A for co-operating with a complementary joint surface 30B defined on the bottom face of the skid 30.

As illustrated in FIG. 2, the surface 21A presents an arcuate profile with its concave side facing downwards. The joint surfaces 21A and 30B are adapted to slide against each other along this curved profile, as represented by arrow $F_1$ in FIG. 2. In frontal section, as shown in FIG. 3, the surface 21A defines a concave central zone $21A_1$ for bearing slideably against a complementary convex zone $30B_3$ of the surface 30A of the skid, and on either side of the zone $21A_1$, medial and lateral convex zones $21A_2$ and $21A_3$ along which complementary concave zones $30B_2$ and $30B_1$ of the surface 30B can bear and slide. In the illustrated embodiment, the central zone $30B_1$ is narrower than the central zone $21A_1$ so as to provide a determined amount of medio-lateral slack between the zones connecting the central zone and the medial and lateral zones $21A_2$ and $30B_2$, and $21A_3$ and $30B_3$. The above-mentioned slack allows the implant 20 and the skid 30 to move relative to each other in a medio-lateral direction, as represented by arrow $F_2$ in FIG. 3.

The prosthesis 1 provides movement very close to that of the natural hinge joint since the skid 30 can move both relative to the tibial implant 10, preferably in a sliding plane-on-plane bearing configuration, and relative to the talus implant 20, performing the movements $F_1$ and $F_2$, which movements may be performed in combination.

A surgical method is described below for implanting the ankle prosthesis 1 of FIGS. 1 to 3, it being understood that the prosthesis 1 in FIGS. 1-3 is merely a non-limiting and illustrative example for the method and the surgical instrument used for implanting the prosthesis. In other words, the method and the instruments described below can be used for implanting ankle prostheses having a wide variety of structures, for example having tibial and/or talus implants that are constituted by a plurality of parts assembled to one another, and that may be made of metal, plastics material, ceramic, composites, and a variety of other materials. In addition, as explained below, the method and the instruments of the invention may also be used for implanting an ankle prosthesis having a stationary skid.

Figure 4:
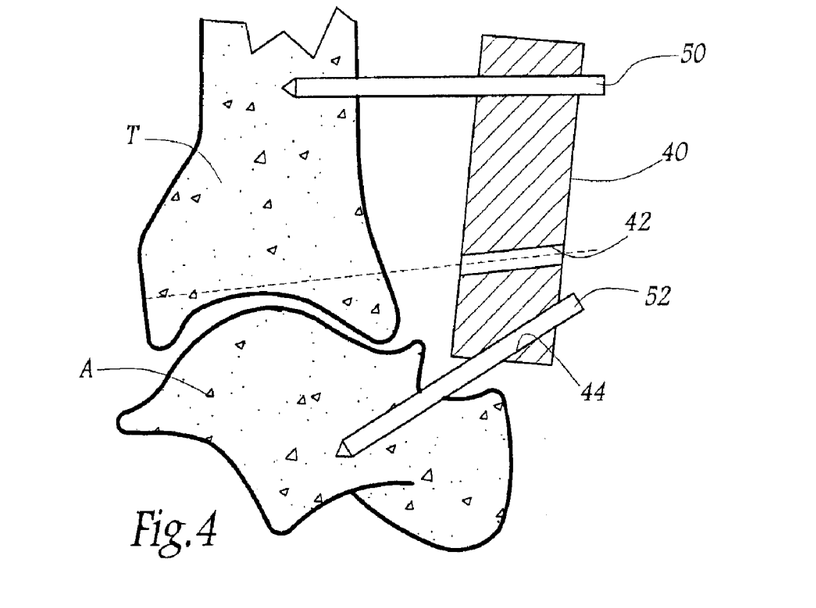
FIGS. 4 and 5 are schematic illustrations of sagittal sections of the tibia and the ankle bone or talus of a patient being prepared to receive an ankle prosthesis in accordance with an embodiment of the present invention.
Figure 5:
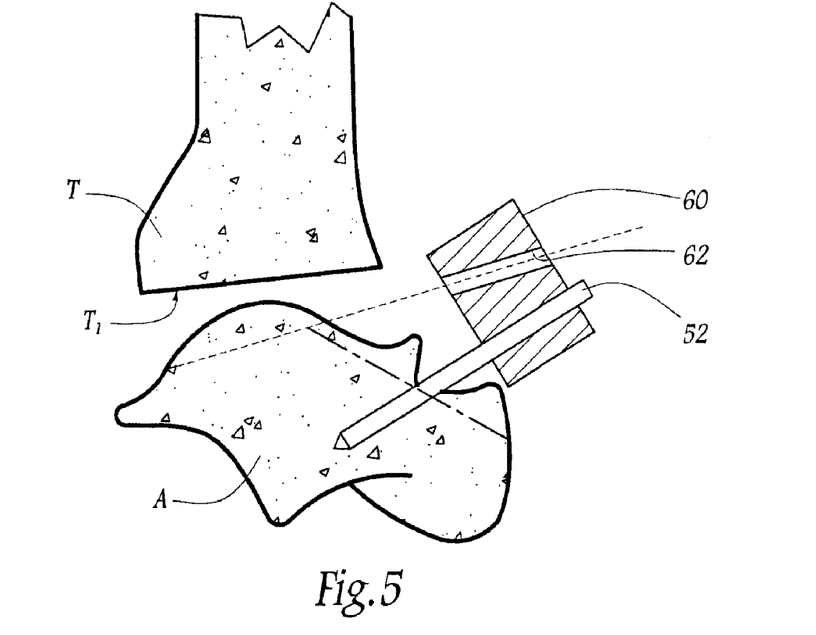
Figure 6:
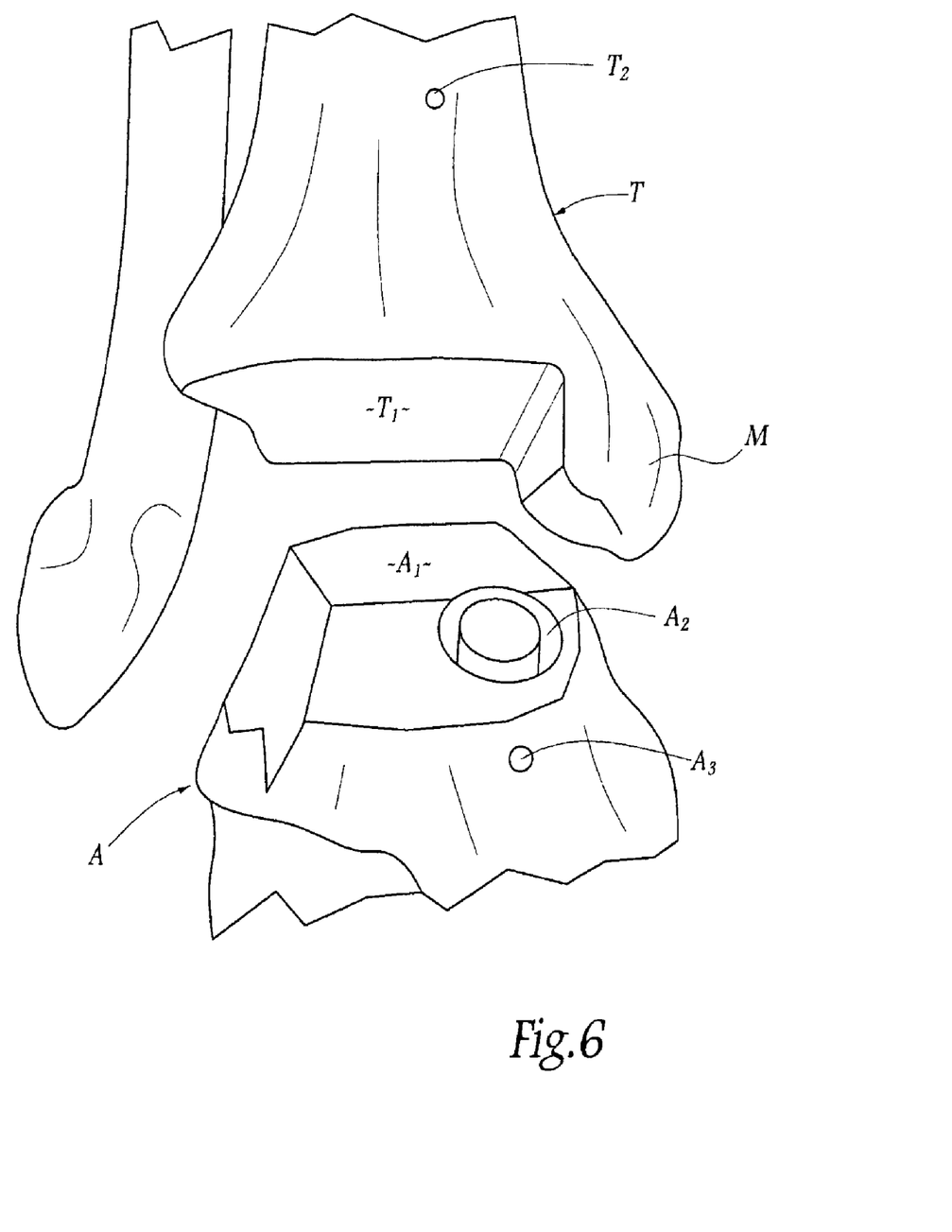
FIG. 6 is a perspective view of the ankle of FIGS. 4 and 5 once all of the preparatory steps have been performed on the bones.

Initially, as shown in FIGS. 4 to 6, the bones of the right ankle of the patient need to be prepared. For this purpose, the surgeon typically uses a first cutting block 40 shown very schematically in FIG. 4, which is held in place on the tibia T of the patient by pin 50 inserted in the tibia in a generally antero-posterior direction. The block 40 defines a slot 42 for passing bone cutter tools, through which the surgeon inserts and guides a cutter blade, for example, so as to resect the bottom end of the tibia T on a line of cut represented by a dashed line in FIG. 4.

The block 40 also defines a bore 44 for passing a pin 52. The bore 44 is positioned so that the pin 52 is anchored in the talus A of the patient. The cutting block 40 is subsequently withdrawn while leaving the pin 52 in place, and a second cutting block 60 is then engaged thereon, as shown in FIG. 5. The block 60 is to enable the talus A to be prepared.

Using the pin 52 thus makes it possible to separate preparing the tibia from preparing the talus, while ensuring that the preparation operations depend on each other. The block 60 defines in particular a slot 62 for passing bone cutter tools, into which the surgeon inserts and guides a blade so as to resect the top end of the talus A, as represented by a dashed line in FIG. 5. With another cutting block that is not shown, likewise fitted on the pin 52 that is left in position in the talus A, the surgeon also resects the top end of the talus on another cutting plane, represented by a chain-dotted line in FIG. 5. Use of the pin 52 thus makes it possible automatically to associate cutting the tibia with cutting the talus both in the sagittal plane of the ankle and in rotation. In the frontal plane, the orientations of these cuts and the thicknesses of bone matter resected can be selected freely by the surgeon.

Other secondary bone preparation operations are typically subsequently performed on the talus A until the tibia T and the talus A are in the state shown in FIG. 6. The embodiment of FIG. 6 shows the plane resected end $T_1$ of the tibia T, and it can be seen that this plane section surface does not extend to the medial side of the ankle, but is interrupted in such a manner as to avoid cutting into the medial malleolus M of the patient. The resected end $A_1$ of the talus A includes a plurality of section planes, i.e. the two main planes shown in FIG. 5, together with a lateral chamfer and a medial chamfer (not shown). Furthermore, in this resected surface $A_1$, a tubular recess $A_2$ is hollowed out, e.g. by means of a bell-shape cutter. Furthermore, the holes left by the pins 50 and 52 are referenced respectively $T_2$ and $A_3$. In a variant that is not shown, the preparation of the ends of the tibia and of the talus includes steps of resurfacing these ends, where necessary.

Figures 7, 8:
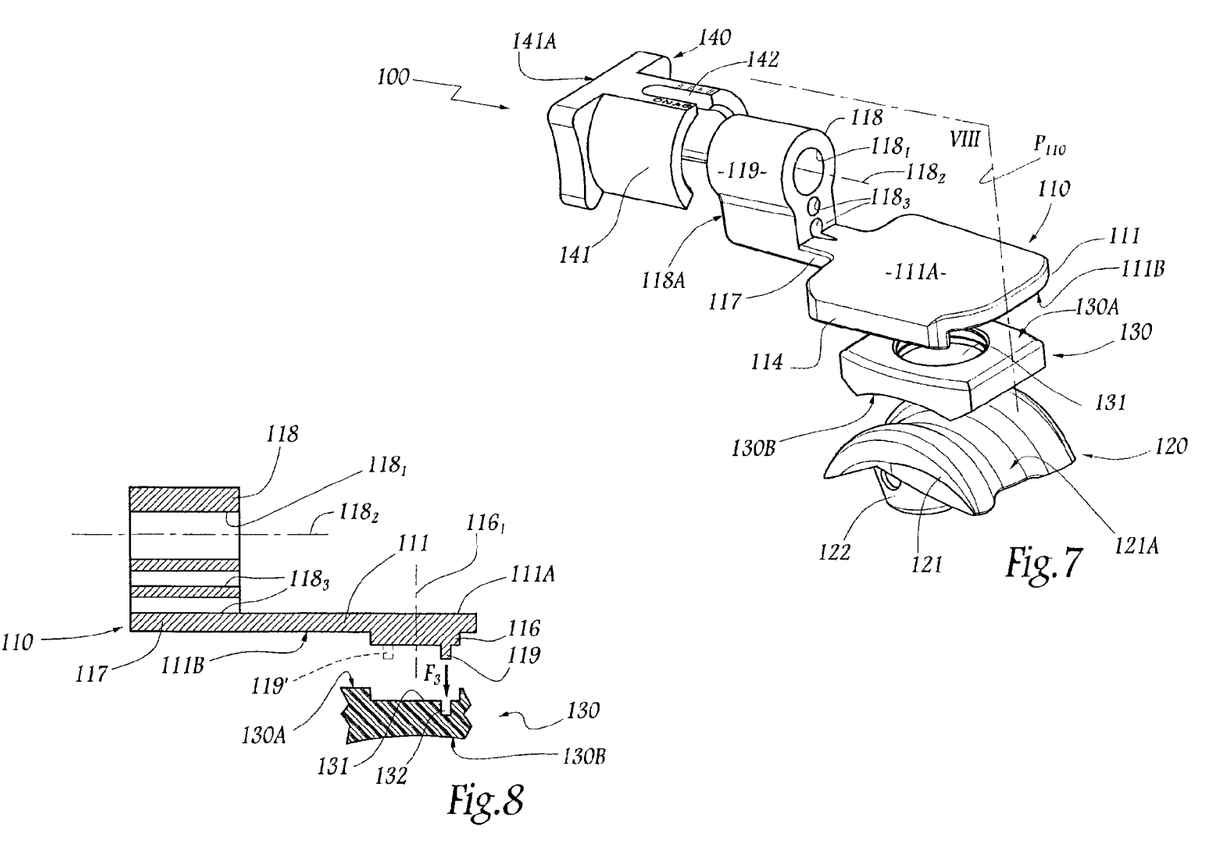
FIG. 7 is an exploded perspective view of one embodiment of a surgical instrumentation kit in accordance with the present invention.
FIG. 8 is a fragmentary section on plane VIII of FIG. 7.

In order to ensure that the various bone preparation operations for implanting the prosthesis 1 are performed appropriately on the tibia T and the talus A, the surgeon makes use of instrumentation kit 100 shown in FIGS. 7 and 8, in accordance with an embodiment of the present invention. The instrumentation kit 100 of this embodiment includes three distinct phantom components, namely a tibial phantom 110, a talus phantom 120, and a phantom skid 130.

In the present embodiment, the component 110 is a phantom of the tibial implant 10. It includes a main plate 111 defining a plane top surface 111A that presents a peripheral outline geometrically analogous to that of the plate 11 of the implant 10 and that is provided, on its medial side, with a rim 114 analogous to the rim 14 of the implant 10. On its bottom face, the plate 111 presents a plane surface 111B from which there extends downwards, in the central zone of this surface, a disk-shaped protrusion 116. In the illustrated embodiment, the protrusions 116 are formed integrally with the remainder of the plate. The central axis $116_1$ of the disk extends perpendicularly to the plate 111, i.e. in a direction that is generally vertical, and is situated substantially in the vertical midplane $P_{110}$ of the plate, which corresponds to the plane VIII shown in FIG. 7.

In one embodiment, in order to ensure that the protrusion 116 is held stationary and more securely in the cavity 131, the peripheral wall of the protrusion may be provided with clip-fastening grooves or other analogous means adapted to co-operate with complementary shapes on the peripheral wall of the cavity 131.

On its anterior side, the plate 111 is extended forwards by a horizontal tab 117 from which there extends vertically upwards a small member 118. Three bores pass through this member 118 in an antero-posterior direction, namely a top bore $118_1$ of longitudinal axis $118_2$, and two lower bores $118_3$ of smaller diameter than the bore $118_1$. The top end of the member 118 presents a generally circularly cylindrical outside surface 119 centered on the axis $118_2$. The axis $118_2$ and the respective longitudinal axes of the lower bores $118_3$ are preferably coplanar and situated substantially in the plane $P_{110}$. In another embodiment, the number of antero-posterior bores passing through the member 118 of the tibial phantom 110 may be less than or greater than three as in the example described. In an alternate embodiment, the member 118 is a separate component releasably attachable to the tibial phantom 110.

Figure 9:
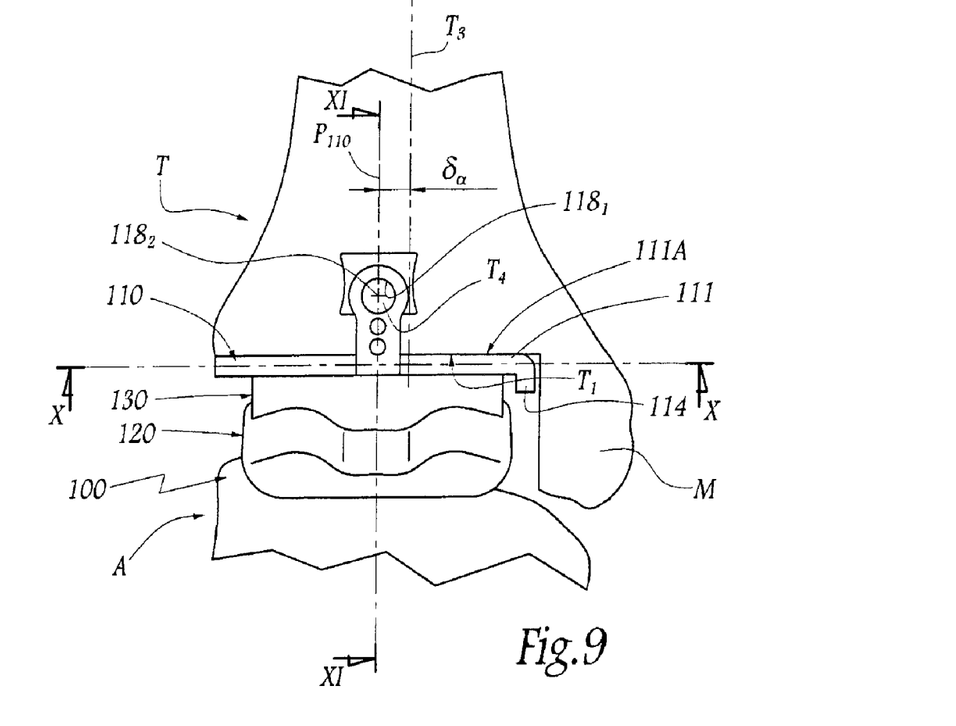
FIG. 9 is an anterior view of the ankle in the FIG. 6 including the surgical instrumentation kit of FIG. 7.

The component 130 is a phantom of the prosthetic skid 30. On its top face, it presents a plane surface 130A with a circularly cylindrical cavity 131 being formed downwards in its central zone. This cavity 131 is complementary to the disk-shaped protrusion 116 of the tibial phantom 110, such that when the phantom skid and the tibial phantom are assembled to each other, as shown in FIG. 9, the protrusion 116 is received in the cavity 131. In order to ensure that this tibial phantom and phantom skid assembly is stationary, in particular in rotation about the axis $116_2$, an eccentric peg 119 projects downwards from the protrusion 116 and is received in a complementary housing 132 formed in the phantom skid 130, in the bottom of the cavity 131, as represented by arrow $F_3$ in FIG. 8. Co-operation between the peg 119 and its housing 132 also seeks to index the angular position between the tibial phantom 110 and the phantom skid 130 so that the vertical midplanes of these components substantially coincide on the plane $P_{110}$, as shown in FIG. 9.

In another example, instead of providing for the phantom skid 130 and the tibial phantom 110 to be two distinct components for assembling to each other in stationary manner, these phantom components could be made as a single part providing the part defines both a plane top surface analogous to the surface 111A and a joint bottom surface analogous to the surface 130B.

On its bottom face, the phantom skid 130 defines a joint surface 130B analogous to the bottom joint surface 30B of the prosthetic skid 30. In complementary manner, a block 121 of the component 120, which constitutes a phantom of the talus implant 20, defines on its top face, a joint surface 121A analogous to the joint surface 21A of the block 21 of the implant 20. As a result, when the phantom skid 130 and the talus phantom 120 co-operate with each other, as in FIG. 9, the surfaces 130B and 121A are jointed one against the other so as to present movement behavior identical to that corresponding to the co-operation between the joint surfaces 30B and 21A of the prosthetic skid 30 and of the talus implant 20. Nevertheless, and preferably, for reasons explained below, no medio-lateral movement of the type associated with the arrow $F_2$ of FIG. 3 is allowed between the phantom skid and the talus phantom. To achieve this, the joint surfaces 121A and 130B are designed to be complementary to each other in horizontal section, ignoring functional clearances. As a result, only overall tilting movement about a medio-lateral axis is possible between the phantom components 120 and 130, with this movement being analogous to the movement associated with arrow $F_1$ in FIG. 2.

On its bottom face, the block 121 of the talus phantom 120 is provided with a hollow bone anchor stud 122 analogous to the stud 22 of the talus implant 20.

In one embodiment of the present method, the surgeon begins by putting the talus phantom 120 in place, by securing its stud 122 in the talus recess $A_2$. Relative to the talus A of the tibia T, the talus phantom then occupies the same position that will subsequently be occupied by the talus implant 20 that is to be implanted.

The surgeon then assembles the tibial phantom 110 and the phantom skid 130, placing the protrusion 116 in the cavity 131 so as to form a one-piece phantom subassembly with no freedom of movement being possible between the tibial phantom and the phantom skid. This phantom subassembly is then put into place in the ankle of the patient, being inserted between the plane resected end $T_1$ of the tibia T and the top joint surface 120B of the talus phantom 120.

Thereafter, the surgeon subjects the ankle joint of the patient to movement, in particular to flexion-extension movements. The talus phantom 120 remains stationary on the top end of the talus A, while the subassembly constituted by the tibial phantom 110 and the phantom skid 130 remains pressed against the resected end $T_1$ of the tibia and is driven freely to move relative to the talus phantom by co-operation between the joint surfaces 130B and 121A, i.e. by performing relative movements analogous to the movement $F_1$ and $F_2$, and preferably analogous to the movement $F_1$ only, as described above with reference to FIGS. 2 and 3.

The above-mentioned phantom subassembly then takes up its position relative to the talus phantom in a manner that is automatic, such that the movements that can be performed between the surfaces 130B and 121A are at a maximum, so as to guarantee that the prosthetic components subsequently implanted in the places of the phantom components will be capable of performing movements of the same order. The capacity of the phantom subassembly to position itself in this way is associated with the freedom of movement allowed between the tibial phantom 110 and the tibia T, by the plane sliding bearing between the top surface 111A of the plate 111 of the phantom and the resected plane bottom end $T_1$ of the tibia. The self-positioning of the tibial phantom 110 simultaneously positions the member 118 that will subsequently be used to position an anchor stud for the tibial implant 10. The kit 100, the tibia T, and the talus A are then in the configuration of FIGS. 9 to 11.

In one embodiment, the instrumentation kit 110 optionally includes a material or a substance for facilitating sliding of the tibial phantom 110 against the end $T_1$ of the tibia during the preoperative movements applied to the ankle; these sliding means may take a wide variety of forms, such as a sliding coating provided on the surface 111A of the tibial phantom or a biocompatible lubricant gel applied on the surface.

Figure 10:
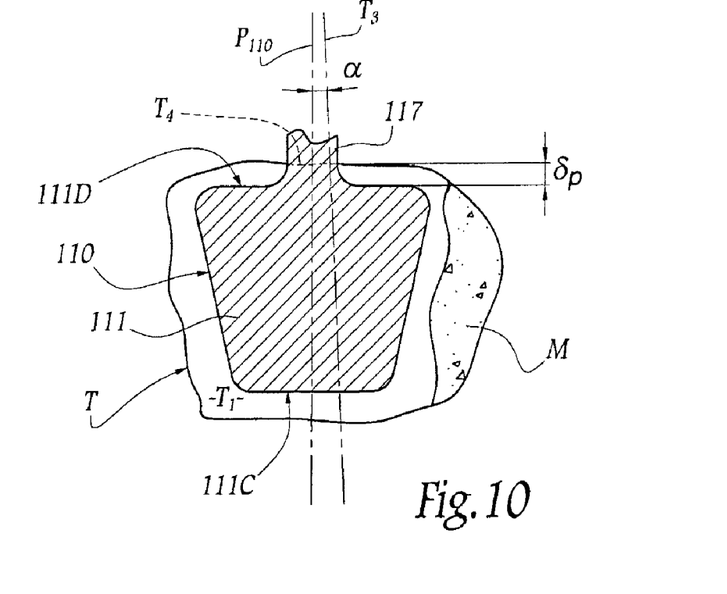
FIGS. 10 and 11 are sections respectively on lines X-X and XI-XI of FIG. 9.

From a geometrical point of view, the tibial phantom 110 is then moved against the end of the tibia $T_1$ so that, for example, its midplane $P_{110}$ is inclined relative to the sagittal plane $T_3$ of the tibia T at a non-zero angle $\alpha$ in horizontal section, as shown in FIG. 10. The anterior zone of the tibia where the bore $118_1$ of the tibial phantom then opens out is referenced $T_4$.

In anterior front view as in FIG. 9, the inclination of the plane $P_{110}$ relative to the plane $T_3$ gives rise to a medio-lateral offset $\delta_\alpha$ at the anterior face of the tibial zone $T_4$.

It will be understood that to avoid disturbing the medio-lateral positioning of the above-mentioned phantom subassembly relative to the tibia T, it may be preferable for no significant medio-lateral movement to be allowed between the phantom skid and the talus phantom, as mentioned above, except insofar as the surgeon takes care to identify the position of the tibial phantom 110 against the end of the tibia $T_1$ after making sure that the surface 130B of the phantom skid occupies a median position in the medio-lateral direction relative to the surface 121A of the talus phantom.

Similarly, the plate 111 of the tibial phantom 110 is then moved rearwards to a greater or lesser extent relative to the end $T_1$ of the tibia T. As a result, the positioning depth p of this plate, e.g. corresponding to the sagittal distance between its posterior edge 111C and the anterior face of the tibial zone $T_4$, is not necessarily equal to the sagittal dimension $d_{111}$ of the plate 111, i.e. the distance between the posterior and anterior edges 111C and 111D of the plate. In the example shown in the figures, this depth p is greater than the dimension $d_{111}$, by an amount written $\delta_p$.

Figure 11:
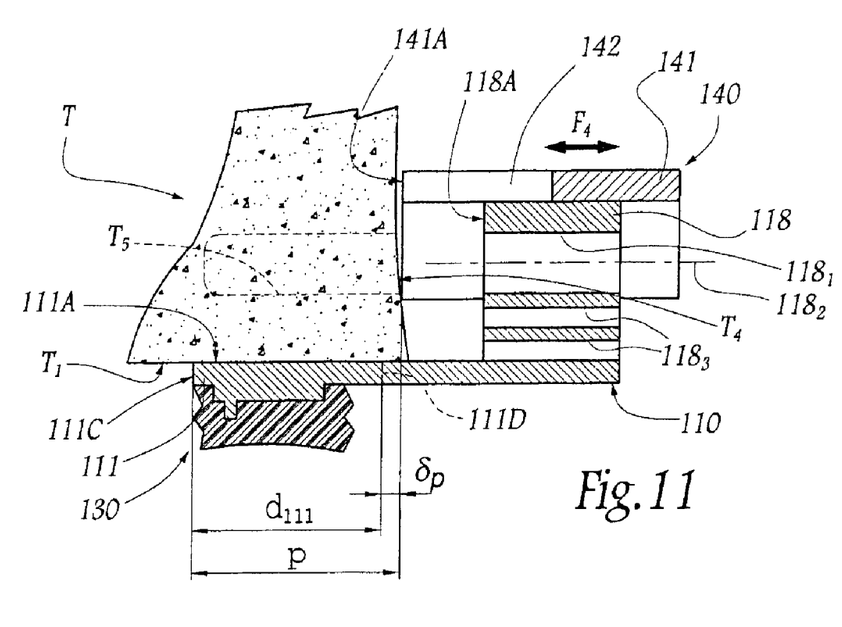

In order to quantify $\delta_p$, i.e. in order to measure the setback position of the plate 111 when offset rearwards from the anterior face of the tibial zone $T_4$, the instrumentation kit 111 advantageously includes a bushing 140 adapted to be slideably fitted on the top end portion of the member 118. By way of example, the bushing 140 thus presents a hollow tubular main body 141 with its inside wall being complementary to the surface 119 of the top end of the member. This body can thus slide along the axis $118_2$ and over the surface 119, as represented by arrow $F_4$, until its posterior edge 141A comes into abutment against the anterior face of the tibial zone $T_4$, as shown in FIG. 11.

In its top face, the body 141 defines an antero-posterior slot 142 along which graduations are provided, such as for example once every two millimeters. By appropriately dimensioning the sagittal dimension between the posterior edge 118A of the member 118 and the posterior edge 111D of the plate 111, the graduation marked "0" of the body 141 in abutment against the tibial zone $T_4$ extends substantially vertically over the edge 118A of the member 118 when the edge 111D is flush with the anterior face of the tibial zone $T_4$ (i.e. when the above-mentioned setback $\delta_p$ is substantially zero), whereas the value of the rearward setback $\delta_p$ of the edge 111D relative to the anterior face of the zone $T_4$ can be measured, where appropriate, by reading the graduation that lies vertically above the edge 118A of the member 118. In the example shown in the figures, the graduation that is read in this way is the graduation marked "2", informing the surgeon that the rearward setback $\delta_p$ of the tibial phantom 110 is equal to about 2 mm.

In another embodiment, instead of using the bushing 140 to identify the antero-posterior position of the tibial phantom 110, the depth position of the phantom can be marked on the end of the tibia, e.g. using a biocompatible ink, it being understood that the surgeon will use the mark made in this way subsequently for positioning the tibial implant in an antero-posterior direction.

After moving the ankle joint of the patient while the phantom components 110, 120, and 130 are placed therein, as described above, the surgeon has reliable information concerning the precise position of the tibial phantom 110 against the resected end $T_1$ of the tibia T. This position is satisfactory or even optimum from the point of view of subsequent dynamic behavior of the implanted prosthesis 1, in the sense that it guarantees that the subsequently implanted skid 30 will be situated facing the central zone of the bottom surface 111B of the tibial implant 10 while taking account of the position in which the talus implant is to be implanted, and providing the tibial implant is in fact implanted in the above-mentioned determined position.

To do this, with the phantom components 110, 120, and 130 held in place in the patient's ankle, the surgeon uses the bore $118_1$ of the tibial phantom 110 to guide the bit of a drill or similar tool in the tibial zone $T_4$. The surgeon thus drills the zone $T_4$ along the axis $118_2$ of the bore $118_1$, with the corresponding hole, represented by a dashed line in FIG. 11 and referenced $T_5$, being made with the angle $\alpha$ relative to the sagittal plane $T_3$ of the tibia T and with the frontal offset $\delta_\alpha$ on the anterior face of the tibia. The hole $T_5$ is to receive the bone anchor stud 13 of the tibial implant 10, so the diameter of the bore $118_1$ is advantageously equal to the outside diameter of the stud 13. The lower bores $118_3$ of the member 118 are subsequently used thereafter to remove at least some of the bone material from the tibial zone $T_4$, so as to make it possible subsequently to slot in the fin 20 of the implant 10 from the front.

Once the hole $T_5$ has been made in the bone, the phantom components 110, 120, and 130 are separated from the ankle, so as to be replaced by the final prosthetic components, i.e. the tibial implant 10, the talus implant 20, and the prosthesis skid 30. The talus implant 10 takes the place of the talus phantom 120.

Figures 12, 13:
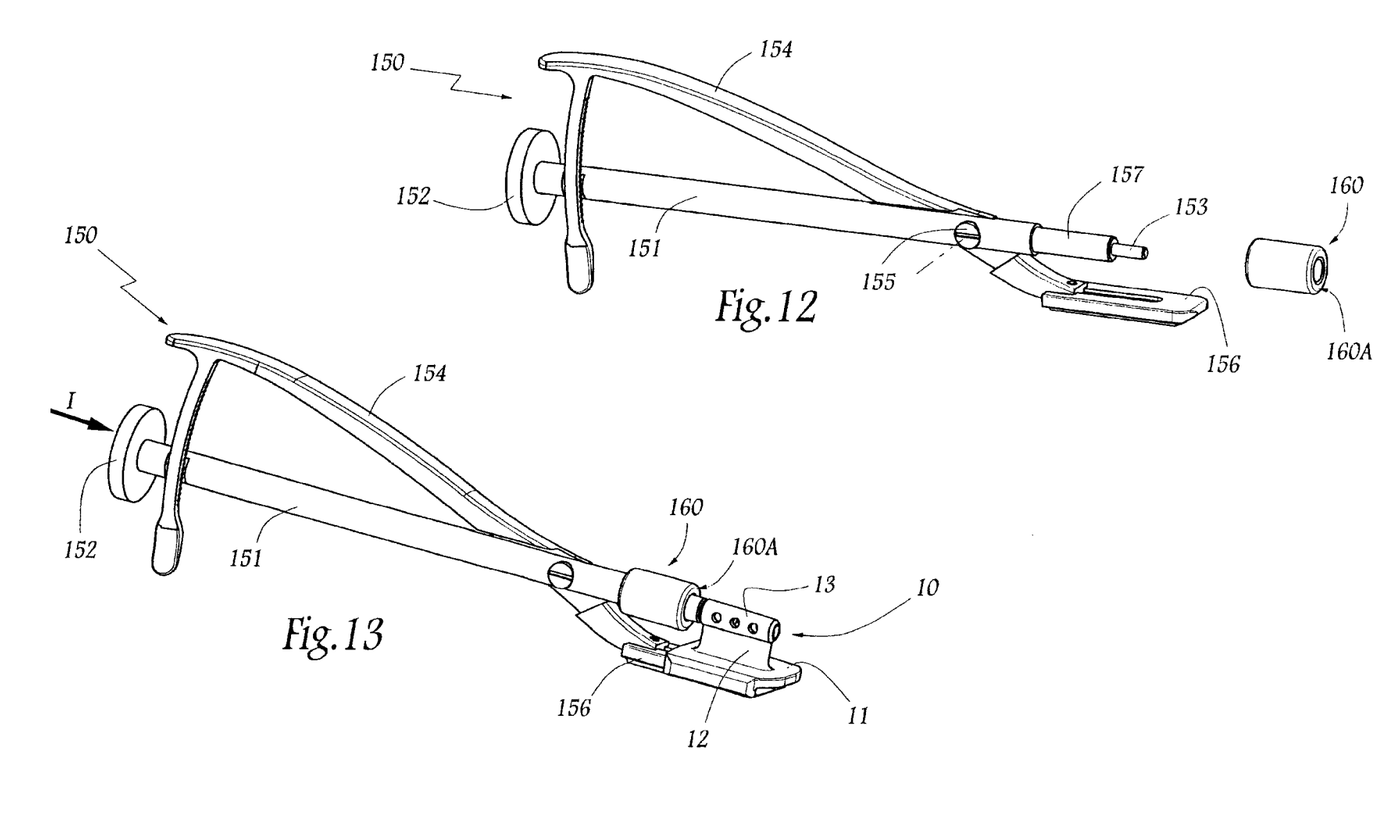
FIG. 12 is a perspective view of an optional instrument for a surgical instrumentation kit in according with the present invention.
FIG. 13 is a perspective view of the instrument of FIG. 12 engaged with a portion of the ankle prosthesis of FIGS. 1-3.
Figure 14:
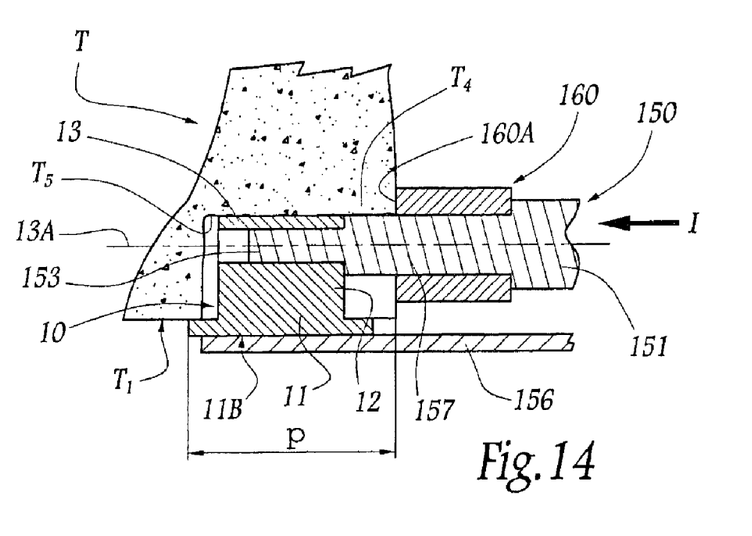
FIG. 14 is a sectional view generally corresponding to FIG. 11, engaged with the instrument of FIG. 13.

In order to implant the tibial implant 10, the surgeon optionally uses the instrument 150 shown in FIGS. 12 and 13 for the purpose of impacting the implant 10 against the epiphyseal end of the tibia T. To do this, the instrument comprises a main impacting rod 151 provided at its proximal end with a head 152 against which impacting forces are applied, and at its distal end with a peg 153 suitable for being engaged in the central bore of the stud 13 of the implant 10, as shown in FIGS. 13 and 14. In order to hold the tibial implant 10 securely while it is being impacted, the instrument 150 includes an implant-clamping branch 154 hinged to the rod 151 like a pair of pliers, about a transverse axis 155. At its distal end, this branch is provided with a plate 156 for bearing against the plane bottom surface 11B of the implant 10. After the peg 153 has been inserted in the stud 13, the plate 156 is caused to press against the surface 11B of the plate 11 by tilting the branch 154 about the axis 155, so as to clamp the implant 10 firmly between the peg and the plate.

Once the implant 10 is held in this way by the instrument 150, the surgeon positions it in the tibial zone $T_4$, and by applying an impacting force I against the head 152, the surgeon forcibly inserts the anchor stud 13 into the hole $T_5$ in the tibia. Since this hole was drilled while taking account of the angle $\alpha$ and of the offset $\delta_\alpha$, the implant 10 is implanted in such a manner that the central axis 13A of its stud 13 occupies substantially the same position relative to the tibia T as was occupied by the axis $118_2$ of the bore $118_1$ of the tibial phantom 110 after the ankle joint fitted with the phantom components had been subjected to movement.

The instrument 150 is also adapted to allow the surgeon to implant the tibial implant 10 with a sagittal depth that is substantially identical to the depth p that was occupied by the tibial phantom 110. For this purpose, the instrument is associated with an insert 160 adapted to be removably fitted around a distal portion 157 of the rod 151, and stepped relative both to the peg 153 and to the remainder of the rod 151. This insert is in the form of a hollow tube whose inside diameter is substantially equal to the outside diameter of the rod portion 157 and whose distal edge 160A is for coming into abutment against the anterior face of the tibia around the hole $T_5$ receiving the tibial anchor stud 13, once the depth p has been reached.

In the preferred embodiment, the longitudinal dimension of the insert 160 is associated with the value $\delta_p$ as measured using the tibial phantom 110, since bringing the edge 160A into abutment against the anterior face of the tibial zone $T_4$ determines the sagittal depth to which the implant 10 can be impacted, as shown in FIG. 14. In practice, the surgeon has at least as many inserts of different lengths as there are graduations on the bushing 140, each insert corresponding to each graduation so that the impacting depth of the tibial implant 10 corresponds to the depth p measured using the bushing.

After the tibial implant 10 has been implanted, the prosthetic skid 30 is placed between the tibial implant and the talus implant 20, being automatically centered against the surface 11B of the tibial implant 10. It can also be understood that if the method and the instrumentation kit 100 are used for implanting an ankle prosthesis having a stationary skid, no extra stress, e.g. associated with off-centering or shear, will be generated in the stationary connection zone between the tibial implant and the skid of the prosthesis. The position in which the tibia implant is implanted at the end of the tibia is specifically determined while taking account of this stationary connection within the ankle joint, in particular relative to the talus implant, since the tibial phantom 110 and the phantom skid 130 are moved in the ankle fitted with the talus implant 120 while they are connected to each other in stationary manner.

The use of the phantom components 110, 120, and 130 presents advantages other than those described above. In particular they make it possible to ensure that the bone preparation operations performed at the bottom end of the tibia T and at the top end of the talus A are satisfactory for the purpose of implanting the ankle prosthesis. In addition, as explained above, the use of these phantom components can make it possible to select the most appropriate size of prosthetic skid for the ankle in question. The surgeon preferably has a plurality of phantom skids analogous to the phantom skid 130 with different thicknesses, such as for example about 4 mm, about 5 mm, about 6 mm, and about 7 mm.

Similarly, a plurality of tibial and/or talus phantoms presenting respective different sizes are preferably made available to the surgeon so as to enable the surgeon to select the sizes for the subsequently implanted implant that are the most appropriate for the patient. It can thus be understood that it is advantageous to be able to assemble and secure a phantom skid 130 of any size with a tibial phantom 110 likewise of any size.

Similarly, the instrumentation kit of the invention may include, in addition to the phantom components used for implanting a right ankle prosthesis such as the prosthesis 1, phantom components for use in inserting a left ankle prosthesis, which may be a moving skid or a stationary skid prosthesis. Under such circumstances, the tibial and talus phantoms used for inserting a left ankle prosthesis are, geometrically symmetrical to the above-described phantom components 110 and 120 about their respective vertical midplanes. Advantageously, the same phantom skid 130 can be used providing it is turned through 180° about the vertical prior to being assembled with the tibial phantom. In practice, the tibial phantom used for inserting a left ankle prosthesis then presents its peg 119' in a position that is diametrically opposite to that of the peg 119 of the tibial phantom 110 used for inserting a right ankle prosthesis, as represented by dashed lines in FIG. 8. In other words, the housing 132 for receiving the peg 119 or the peg 119' is used for keying purposes when assembling the tibial phantom with the phantom skid, depending on whether the prosthesis for insertion is a right ankle prosthesis or a left ankle prosthesis.

Various arrangements and variants of the surgical instrumentation kit 100 and of the insertion method described above can also be envisaged. It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

For example, instead of providing for the phantom components to be used exclusively for preoperative testing and checking purposes, it is possible to use prosthetic components during testing and checking, or at least portions of prosthetic elements, and then once the checking and testing has been completed, these components or portions are used in full or in part as implants for being implanted permanently in the ankle. This alternative embodiment applies for example when it is desired to revise an ankle prosthesis that has already been implanted, in which case the talus implant is used as a phantom during testing and checking, together with a tibial phantom and a phantom skid, in order to implant a new tibial implant and a new prosthetic skid.

What is claimed is:

1. A surgical instrument for implanting at least a tibial prosthesis on a prepared bottom end of a tibia and a talus prosthesis on a prepared top surface of a talus of an ankle joint, the surgical instrument comprising:
    at least one tibial phantom generally corresponding to at least some geometric features of the tibial prosthesis, the tibial phantom comprising a top surface adapted to move freely against the prepared bottom end of the tibia;
    at least one talus phantom generally corresponding to at least some geometric features of the talus prosthesis, the talus phantom adapted to engage with the prepared top surface of the talus; and
    at least one phantom skid located between the tibial phantom and the talus phantom, the phantom skid engaged with the tibial phantom with no freedom of movement between the tibial phantom and the phantom skid, such that dynamic engagement between the phantom skid and the talus phantom through extension and flexion of the ankle joint positions the tibial phantom relative to the prepared bottom end of the tibia.

2. The surgical instrument of claim 1 wherein the tibial phantom and the phantom skid comprise separate components.

3. The surgical instrument of claim 1 wherein the tibial phantom and the phantom skid comprise a single component.

4. The surgical instrument of claim 1 wherein the tibial phantom is displaced along the prepared bottom end of the tibia during extension and flexion of the ankle joint to a location corresponding to natural movement of the ankle joint.

5. The surgical instrument of claim 1 comprising a low friction coating located on the top surface of the tibial phantom.

6. The surgical instrument of claim 1 comprising a biocompatible lubricant located between the top surface of the tibial phantom and the prepared bottom end of the tibia.

7. The surgical instrument of claim 1 wherein extension and flexion of the ankle joint moves a midplane of the tibial phantom to an angle α relative to a sagittal plane $T_3$ of the ankle joint.

8. The surgical instrument of claim 1 wherein an upper surface of the talus phantom and a bottom surface of the phantom skid comprise complementary surfaces that simulate movement of the talus prosthesis and a prosthetic skid in the ankle joint.

9. The surgical instrument of claim 1 comprising an alignment member that is simultaneously positioned relative to the tibia during positioning of the tibial phantom.

10. The surgical instrument of claim 1 comprising an alignment member engaged with the tibial phantom, the alignment member including a drill guide adapted to prepare the tibia to receive the tibial prosthesis.

11. The surgical instrument of claim 1 comprising an alignment member engaged to the tibial phantom that is positioned opposite an anterior face of the tibia.

12. The surgical instrument of claim 1 comprising an alignment member that measures a setback of the tibial phantom relative to a surface of the tibia.

13. The surgical instrument of claim 1 comprising an alignment member engaged with the tibial phantom that measures a setback ($\delta_p$) of the tibial phantom relative to an anterior surface of the tibia.

14. The surgical instrument of claim 1 comprising an alignment member attached to the tibial phantom, at least a portion of the alignment guide and the tibial phantom comprising a single component.

15. The surgical instrument of claim 1 wherein displacement of a midplane of the tibial phantom to an angle α relative to a sagittal plane ($T_3$) of the ankle joint results in a mediolateral offset ($\delta_\alpha$) of an alignment member along an anterior face of the tibia.

16. The surgical instrument of claim 1 wherein the dynamic engagement between the phantom skid and the talus phantom self-positions the tibial phantom on the prepared bottom end of the tibia in a precise anatomical location corresponding to an optimum operation of the ankle joint.

17. The surgical instrument of claim 1 comprising a kit including one or more of a plurality of tibial phantoms, a plurality of talus phantoms, and a plurality of phantom skids.

18. The surgical instrument of claim 1 comprising:
    an alignment feature engaged with the tibial phantom adapted to prepare the tibia to receive the tibial prosthesis; and
    an impacting instrument that locates the tibial prosthesis at a setback relative to a surface of the tibia.

19. The surgical instrument of claim 1 comprising:
    an alignment feature engaged with the tibial phantom adapted to determine a setback of the tibial prosthesis relative to a surface of the tibia; and
    an impacting instrument that implants the tibial prosthesis in the tibia at the determined setback.

20. The surgical instrument of claim 1 comprising:
    an alignment feature engaged with the tibial phantom adapted to determine a setback of the tibial prosthesis relative to an anterior surface of the tibia; and
    an impacting instrument that implants the tibial prosthesis in the tibia at the determined setback.

21. The surgical instrument of claim 1 comprising:
    an alignment feature engaged with the tibial phantom adapted to determine a setback of the tibial prosthesis relative to a surface of the tibia; and
    an impacting instrument comprising an insert that contacts a surface of the tibia when the tibial prosthesis is in the tibia at the setback.

22. The surgical instrument of claim 1 comprising an impacting instrument that locates the tibial prosthesis at a setback relative to a surface of the tibia.

23. A surgical system comprising:
- a tibial prosthesis configured for implantation on a prepared bottom end of a tibia, the tibial prosthesis comprising a top surface with a bone anchor stud protruding therefrom, the bone anchor stud configured for insertion into the prepared bottom end of the tibia;
- a talus prosthesis configured for implantation on a prepared top surface of a talus of an ankle joint;
- a skid configured for implantation between the tibial prosthesis and the talus prosthesis;
- a tibial phantom generally corresponding to at least some geometric features of the tibial prosthesis, the tibial phantom comprising a top surface adapted to move freely against the prepared bottom end of the tibia;
- a talus phantom generally corresponding to at least some geometric features of the talus prosthesis, the talus phantom adapted to engage with the prepared top surface of the talus; and
- a phantom skid located between the tibial phantom and the talus phantom, wherein movement of the phantom skid with respect to the tibial phantom is at least partially constrained in a manner in which movement of the skid with respect to the tibial prosthesis is not constrained, such that dynamic engagement between the phantom skid and the talus phantom through extension and flexion of the ankle joint positions the tibial phantom relative to the prepared bottom end of the tibia in a phantom position indicating an implant position for the tibial prosthesis.

24. The surgical system of claim 23, wherein the prepared bottom surface of the tibia and the top surface of the tibial phantom are substantially flat, such that the prepared bottom surface of the tibia slides against the top surface of the tibial phantom.

25. The surgical system of claim 23, further comprising an alignment member engaged with the tibial phantom, the alignment member configured to indicate, when the tibial phantom is in the phantom position, a location of the bone anchor stud corresponding to the tibial prosthesis being in the implant position.

26. A surgical instrumentation kit for fitting an ankle prosthesis, the ankle prosthesis including a tibial implant, a talar implant and a prosthetic bearing interposed between the tibial and talar implants, the surgical instrumentation kit comprising:
- a tibial phantom of the tibial implant;
- a talar phantom of the talar implant; and
- a phantom bearing of the prosthetic bearing, wherein the tibial phantom, the talar phantom, and the phantom bearing are adapted to be stressed jointly in a region of an ankle of a patient undergoing surgery, for preoperative testing and checking, wherein the tibial phantom is adapted to be both fixedly connected to the phantom bearing and freely displaceable against a lower end of the patient's tibia.

27. The surgical instrumentation kit of claim 26, wherein the talar phantom is adapted to display kinematic characteristics, with respect to the phantom bearing and the patient's talus, which are at least partly analogous to those of the talar implant with respect to the prosthetic bearing and the patient's talus.

28. The surgical instrumentation kit of claim 27, wherein articular surfaces of the talar phantom and of the phantom bearing are adapted to cooperate with each other, and are complementary to each other in horizontal section.

29. The surgical instrumentation kit of claim 26, wherein the tibial phantom and the phantom bearing are distinct components capable of being assembled to each other, respectively provided with means for fixing and immobilizing one on the other.

30. The surgical instrumentation kit of claim 29, wherein the means of the tibial phantom and of the phantom bearing are adapted to cooperate together by complementarity of shapes.

31. The surgical instrumentation kit of claim 29, further comprising, on one hand, two tibial phantoms, respectively adapted to be used for fitting a right ankle prosthesis and a left ankle prosthesis, and, on the other hand, two talar phantoms, respectively adapted to be used for fitting a right ankle prosthesis and a left ankle prosthesis, wherein the same phantom bearing is adapted to be used equally well with either the tibial phantom and talar phantom associated with the right ankle prosthesis, or the tibial phantom and talar phantom associated with the left ankle prosthesis, and wherein the means are adapted to key assembly of the same phantom bearing with either of the two tibial phantoms.

32. The surgical instrumentation kit of claim 26, wherein the tibial phantom and the phantom bearing are made as a single part.

33. The surgical instrumentation kit of claim 26, further comprising a means for locating a given position occupied by the tibial phantom against the end of the tibia after said stressing of the tibial phantom, the talar phantom, and the phantom bearing in the region of the ankle.

34. The surgical instrumentation kit of claim 33, wherein the tibial phantom includes the means for locating.

35. The surgical instrumentation kit of claim 33, wherein the means for locating comprises a means for guiding a tool for drilling or cutting the tibia, wherein the means is adapted to apply such tool in the tibia with an angle and an offset with respect to a predetermined plane of the tibia, wherein the angle and the offset are associated with the given position, wherein the angle is a horizontal angle, wherein the plane is a sagittal plane of the tibia, and wherein the offset is a mediolateral offset with respect to the sagittal plane.

36. The surgical instrumentation kit of claim 33, wherein the means for locating comprises a means for measuring depth of the given position with respect to an anterior face of the tibia.

37. The surgical instrumentation kit of claim 36, further comprising an accessory for impacting the tibial implant and an insert adapted to be fitted on the instrument so as to abut the anterior face of the tibia when the tibial implant occupies a position with respect to the end of the tibia, a depth of which is substantially equal to the depth of the given position.

38. The surgical instrumentation kit of claim 26, further comprising a means for sliding between the lower end of the tibia and a surface of the tibial phantom, wherein the means for sliding is adapted to be displaceably pressed against the lower end of the tibia.

* * * * *